(12) United States Patent
Beverini et al.

(10) Patent No.: US 8,709,783 B2
(45) Date of Patent: Apr. 29, 2014

(54) PROBIOTIC ENRICHED AND LOW ORGANIC ACID FOOD PRODUCTS

(75) Inventors: Marc Beverini, Chatenay Malabry (FR); Christelle Lacorre, Etampes (FR); Alan Francois, Chevannes (FR); Mickael Labbe, Montlhery (FR)

(73) Assignee: Compagnie Gervais Danone, Paris (FR)

( * ) Notice: Subject to any disclaimer, the term of this patent is extended or adjusted under 35 U.S.C. 154(b) by 108 days.

(21) Appl. No.: 13/224,716

(22) Filed: Sep. 2, 2011

(65) Prior Publication Data

US 2012/0058540 A1 Mar. 8, 2012

Related U.S. Application Data

(62) Division of application No. 11/916,903, filed as application No. PCT/EP2006/063109 on Jun. 12, 2006.

(30) Foreign Application Priority Data

Jun. 10, 2005 (FR) ...................................... 05 05911

(51) Int. Cl.
*C12N 1/20* (2006.01)
(52) U.S. Cl.
USPC ........................................ 435/252.9; 435/857
(58) Field of Classification Search
USPC ...................................................... 435/252.9
See application file for complete search history.

(56) References Cited

U.S. PATENT DOCUMENTS

| 1,417,412 A | 5/1922 | Richard |
| 2003/0026884 A1 | 2/2003 | Mantius et al. |
| 2003/0091694 A1 | 5/2003 | Remo |
| 2004/0197448 A1 | 10/2004 | Chung et al. |

FOREIGN PATENT DOCUMENTS

| EP | 0 113 055 | 7/1984 |
| EP | 0 166 238 | 1/1986 |
| EP | 0244903 A1 | 11/1987 |
| FR | 2 858 630 | 2/2005 |
| JP | 63 251070 | 10/1988 |
| SU | 1465451 | 3/1989 |
| WO | WO 00/70972 | 11/2000 |

OTHER PUBLICATIONS

Lu et al. "Differential Glucose and Fructose Utilization During Cucumber Juice Fermentation" Journal of Food Science—vol. 66, No. 1, 2001, pp. 162-166*
Palles et al. "Citrate metabolism in *Lactobacillus casei* and *Lactobacillus plantarum*" Journal of Applied Microbiology 1998, 85, 147-154.*
Radler et al. "The Metabolism of Several Carboxylic Acids by Lactic Acid Bacteria" Z Lebensm Unters Forsch 1984, 179:228-231.*
International Search Report for PCT/EP2006/063109 filed Jun. 12, 2006, 3 pgs.
AOAC Official Methods of Analysis (1984), Solids; Conductance-Temperature Correlation for Processed Raisins; p. 417.
AOAC Official Methods of Analysis (1984), Sugars and Sugar Products; p. 575.
Hartwig, Pam and McDaniel, Mina R.; "Flavor Characteristics of Lactic, Malic, Citric, and Acetic Acids at Various pH Levels"; Journal of Food Science, vol. 60, No. 2, 1995; pp. 384-388.
Hegazi, F.Z. and Abo-Elnaga, I.G.; "Degradation of Organic Acids by Dairy Lactic Acid Bateria"; Zbl. Bakt, IT, Abt. 135 (1980), 212-222; Dairy Department, Faculty of Agriculture, University of Assiut, Assiut, Egypt.
Van Beek, Sylvie and Priest, Fergus G.; "Decarboxylation of Substituted Cinnamic Acids by Lactic Acid Bacteria Isolated during Malt Whisky Fermentation"; Applied and Environment Microbiology, Dec. 2000, p. 5322-5328.
United States Office Action for U.S. Appl. No. 11/916,903, dated Jun. 24, 2013.

\* cited by examiner

*Primary Examiner* — Thane Underdahl
(74) *Attorney, Agent, or Firm* — Alston & Bird LLP (57) ABSTRACT

This invention relates to a fruit-based food product such as beverages or fruit purees, comprising a concentration of live and stable probiotics, which is preferably greater than $10^8$ CFU/ml, a high fruit content, which is preferably greater than 50%, and a low organic acid content, and wherein the production of off-tastes is reduced or diminished in relation to the initial fruit matrix, as well as method for preparing a food product such as this.

1 Claim, 1 Drawing Sheet

PROBIOTIC ENRICHED AND LOW ORGANIC ACID FOOD PRODUCTS

CROSS REFERENCE TO RELATED APPLICATIONS

This application is a divisional application of application Ser. No. 11/916,903, filed Dec. 7, 2007, which is a national stage application filed under 35 U.S.C. 371 of International Application No. PCT/EP2006/063109, filed Jun. 12, 2006, which claims priority from French Application No. 0505911, filed Jun. 10, 2005.

FIELD OF THE INVENTION

This invention relates to a fruit-based food product such as beverages or fruit purees, comprising a concentration of live and stable probiotics, which is preferably greater than $10^8$ CFU/ml, a high fruit content, which is preferably greater than 50% and the organic acid content of which is reduced by 10 to 100%, preferably by 30 to 70%, and more preferably yet by 60%, in relation to the initial organic acid content of the fruit matrix, as well as a method for preparing a food product such as this.

BACKGROUND

The ingestion of live microorganisms called probiotics, some of which are bacteria, and in particular those which belong to the genus *Lactobacillus*, are particularly beneficial to one's health. As a matter of fact, they have been the subject matter of numerous studies demonstrating preventive clinical effects in various fields (e.g., in the fields of allergic manifestations, infectious diarrhoea and inflammatory diseases) and on certain physiological functions (e.g., the digestion of lactose, bowel transit and immunity). These probiotics are, in particular, capable of promoting proper functioning of intestinal flora, which are likely to affect the overall population. As a matter of fact, among other things, these bacteria produce other bacteriocins and lactic acid, which indirectly increase the digestibility of food products, promote intestinal peristalsis, and accelerate the evacuation of stools. Furthermore, these bacteria produce certain B-complex vitamins, and in general promote the absorption of vitamins and minerals, reduce blood cholesterol, strengthen the immune system and coat the mucous membranes of the intestines so as to protect against the invasion and activities of harmful microorganisms.

For this reason, the agroprocessing industries have been attempting for several years to incorporate such bacteria into their products.

Such products with added bacteria are traditionally dairy products, however, there is an advantage for the agroprocessing industry to develop other food products, particularly fruit-based ones.

Other fruit-based food products with added bacteria of the *Lactobacillus* type are already known in the prior art, e.g., in the international patent application WO 00/70972, and the European patent application EP 0113055.

However, it has been possible to observe bacterial growth in food products to which lactobacilli have been added, which, during storage of the products, results in the qualities thereof being altered by the production of gases and off-tastes, thereby making them unsuitable for consumption.

Numerous microorganisms are capable of decarboxylating substituted cinnamic acids such as trans-4-hydroxy-methoxy-cinnamic acid (ferulic acid) and trans-4-hydroxy-cinnamic acid (p-coumaric acid), in order to form the two following volatile compounds, respectively:

3-methoxy-4-hydroxystyrene (4-vinyl guaiacol) and 4-hydroxystyrene (4-vinyl phenol). These molecules are responsible for off-tastes of the "phenol, smoky, glove-like and medicinal" type. P-coumaric acid and decarboxylated ferulic acid activity was detected in bacteria of the *Lactobacillus* type. In particular, the lactobacilli known for these activities are as follows: *L. brevis, L. crispatus, L. fermentum, L. plantarum, L. pentosus* and *L. paracasei* (bibliog. Ref.: Van Beek, S and Priest FG-2000—"Decarboxylation of substituted cinnamic acids by lactic acid bacteria isolated during malt whisky fermentation—*Applied and Environmental Microbiology*, 66 (12): 5322-8). Strains of lactobacilli are thus capable of producing off-tastes from phenolic acids via biotransformation pathways.

At present, the solutions proposed in the prior art for solving this problem involving the production of gases and off-tastes consist of preserving the products at a temperature of between 4 and 8° C. and with a low fruit concentration (approximately 25%), for example, as in the international patent application WO 00/70972, filed by the PROBI company.

However, these solutions do not make it possible to propose products having a fruit concentration greater than 50%, and further comprising a significant concentration of live and stable bacteria of the *Lactobillus* genus. A significant concentration is understood to mean a population greater than or equal to $10^8$ CFU/ml of product. Stable bacteria are understood to mean a bacterial population having reduced metabolic activity (production of gases and/or off-tastes, and acidification during limited and controlled storage conditions) when cold, i.e., at a temperature of between 4 and 10° C. The limited post-acidification is the result of a reduction in the concentration of organic acids present in the product, on the one hand, and, on the other hand, the low storage temperature of said product.

A fruit-based food product which is of the beverage or fruit puree type and which comprises stable, live probiotics, will have the advantage of providing the consumer with the benefits of fruits and probiotics.

The National Plan on Nutrition and Health advocates consumption of a minimum of five portions of fruits and vegetable per day. Observations conducted by numerous scientists show that consuming more fruits and vegetables makes it possible in particular, to reduce the cholesterol rate and lipid intake, and to limit the prevalence of obesity in children.

Several scientific studies suggest that probiotics can likewise play a leading role with regards to health. Each probiotic strain can offer specific health benefits. Among these benefits can be found: improved digestive system functioning and strengthened natural defenses. Some probiotics act by absorbing proteins and others produce vitamins. Some can likewise produce compounds that fight against the propagation of pathogenic bacteria and can therefore play a role in the intestinal ecosystem.

It would be desirable for the agroprocessing industry to be capable of preparing such food products, and that is the subject matter of this invention.

In order to increase the viability of bacteria, the European patent applications EP 0113055 and EP 0166238, filed by Kirin Beer, propose that the concentration of polyphenols in fruit juices, which are bacteriostatic components, be selectively reduced by placing the juices in contact with absorbing agents. In this case, the desired objective is to also promote fermentation of the bacteria and to not keep the initial population stable, as is the case according to this invention.

It is known in the prior art that fruits contain organic acids, and the inventors have observed that bacteria of the *Lactobacillus* genus metabolize these organic acids, and that this metabolization of organic acids can be responsible for the production of carbon dioxide and/or off-tastes in fruit-based products. The organic acid compositions of some fruits can also be known by consulting bibliographic sources, e.g., such as the acidity ranges per fruit in the "Code of Practice" of the A.I.J.N.

Numerous strains of the *Leuconostoc, Streptococcus* and *Lactobacillus* genera are capable of degrading malate, citrate, pyruvate, fumarate, tartrate and gluconate in order to produce gases. In comparison to the measurement of gas produced, the determination of diacetyl and acetoin contents is a more effective method for detecting pyruvate degradation (Hegazi, F. Z., Abo-Elnaga, I. G., 1980. "Degradation of organic acids by dairy lactic acid bacteria. *Mikrobioligie der Landwirtshaft der Technologie and des Umweltschutzes,* 135 (3), 212).

When degraded, organic acids such as malic acid or citric acid do not, as a matter of fact, present the consumer with these problematics involving the generation of unpleasant tastes, unless this assimilation is accompanied by an excessively high production of acetate, which also produces off-tastes. However, the assimilation of these organic acids by bacterial strains will in this case produce $CO_2$, which will inflate the product packaging. As a matter of fact, these organic acids are metabolized naturally by certain species of lactobacilli, in order to produce pyruvate (the principal compound of metabolic cycles such as carbonaceous metabolism) and $CO_2$; furthermore, pyruvate is itself subject to decarboxylation reactions, thus proportionally increasing the rates of $CO_2$ produced.

Some of these organic acids are phenolic compounds (coumaric acid, ferulic acid) and the degradation of these compounds by bacterial strains may produce off-tastes in the product.

Depending on the pH of the end product, the sensory profile of an acid is highly variable. Thus, lactic acid is more astringent at pH 3.5 in comparison to citric acid and malic acid (Hartwig, P., McDaniel, M. R., 1995. "Flavor characteristics of lactic, malic, citric and acetic acids at various pH levels." *Journal of Food Science,* 60 (2), 384-388.).

Figure 1:
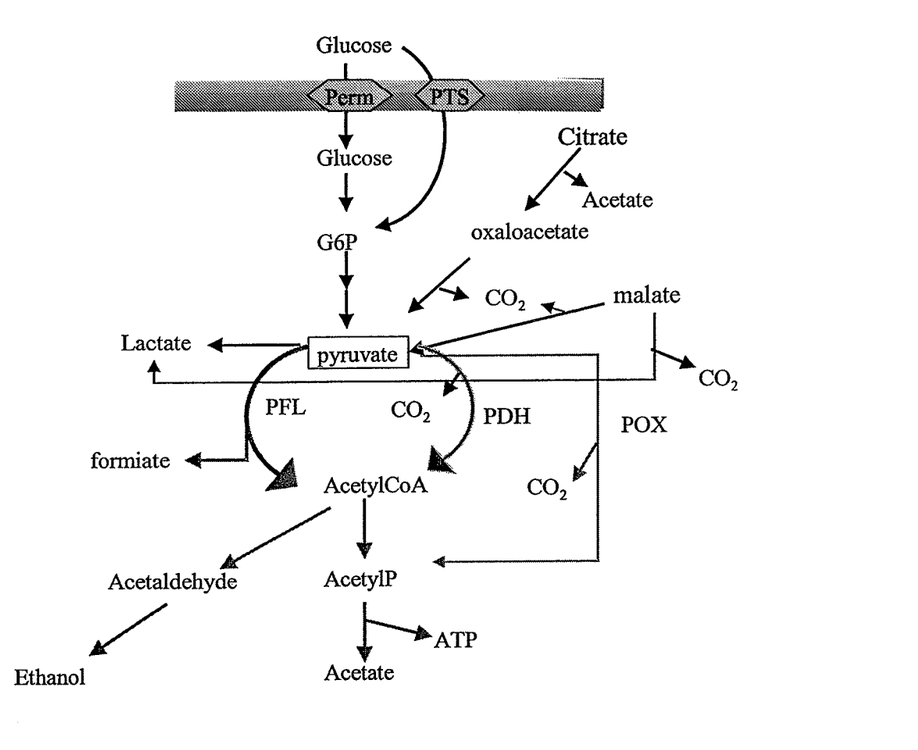
FIG. 1 is a diagram of the metabolic assimilation of citrate and malate, and of the production of acetate in lactic bacteria.

FIG. 1 thus shows the mechanism of metabolism for malic acid (or malate), citric acid (or citrate) and pyruvate.

Commercial beverages exist, in particular the product ProViva® distributed by Skånemejerier, which contain a strain of the *Lactobacillus* genus at a maximum concentration equal to $10^8$ CFU/ml and at an acid pH (pH=3.8). However, the stability of the product is only guaranteed when stored at 4° C. and as the result of a low concentration of fruit juices (<25%). Furthermore, the ProViva® commercial products have targeted certain types of fruits which have low organic acid concentrations and which do not include major juices like orange juice, apple juice and exotic multi-fruit juices.

SUMMARY

The inventors have shown that depletion of organic acids from the matrix of fruits on which the food product is based makes it possible to reduce or eliminate the production of carbon dioxide and/or off-tastes from the final food product, after packaging, while at the same time protecting the nutritional qualities of the product, regardless of the fruit, fruit concentration and organic acid concentration of the end product. Thus, the inventors propose to control and recommend a limiting organic acid concentration that must be adjusted to the fruit matrix target concentration in the formula and to the type of fruit in question.

One object of this invention, therefore, is a packaged fruit-based food product comprising live and stable probiotics and the organic acid content of which is reduced by 10 to 100%, preferably 30 to 70%, and more preferably still by 60% in relation to the initial organic acid content of the fruit matrix, and wherein the production of off-tastes is reduced or eliminated in comparison to the initial fruit matrix.

DETAILED DESCRIPTION

The term probiotic is meant to designate live microorganisms which, when incorporated in a sufficient quantity, have a positive effect on health, beyond traditional nutritional effects.

According to this invention, the term live probiotics is meant to designate probiotics for which the survival rate after 29 days in a food product according to this invention is greater than 60%, and advantageously greater than 80%.

The viability of probiotics is measured by counting techniques known to those skilled in the art, e.g., such as mass counting, surface counting, Malassez cells, direct counting, turbidity, nephelometry, electronic counting, flow cytometry, fluorescence, impedance measurement and image analysis.

According to this invention the term stable probiotics is meant to designate probiotics having an absence of activity for at least 30 days at 10° C. The absence of activity results in:
An absence of detection of gas production (e.g., $CO_2$) during packaged storage,
A constant organoleptic quality without any alteration of the initial qualities of the fruit matrix and without any production of off-tastes,
An absence of significant post-acidification (decrease in pH<0.5 unit),
A non-proliferation of the probiotics and retention of the initial population (±50%).
In particular, these probiotics can be bacteria.

According to this invention, the term bacteria is understood to preferably designate lactic bacteria, of the genera *Lactobacillus* spp., *Bifidobacterium* spp., *Streptococcus* spp., *Lactococcus* spp., *Leuconostoc* spp. and, in particular, *Lactobacillus casei, Lactobacillus plantarum, Lactobacillus bulgaricus, Lactobacillus helveticus, Lactobacillus aciophilus, Bifidobacterium animalis, Bifidobacterium breve, Streptococcus thermophilus* and *Lactococcus lactis.*

More particularly, the preferred bacteria according to this invention are bacteria having the capacity to degrade organic acids into $CO_2$ and/or into compounds producing off-tastes.

More particularly, the preferred bacterial strains according to this invention are of the genus *Lactobacillus,* preferably *Lactobacillus plantarum* and *Lactobacillus casei,* and more preferably yet the *Lactobacillus plantarum* strains deposited at the Deutsche Sammlung von Mikrooganismen von Zelkuturen GmbH on 16 Mar. 1995, under the number DSM 9843, or strains of *Lactobacillus plantarum* deposited at the Collection Nationale des Cultures de Microorganismes, 25 rue du Docteur Roux, Paris, FRANCE on Apr. 4, 2002, under the number CNCM I-2845.

The *Lactobacillus plantarum* strain deposited at the Deutsche Sammlung von Mikrooganismen von Zelkuturen GmbH on 16 Mar. 1995, under the number DSM 9843 is marketed by the PROBI company, under the name *Lactobacillus plantarum* 299v®. This strain has numerous advantages for use as a probiotic in a fruit-based food product:

It meets the probiotic criteria established by the scientific community.

It is patented, characterised (RAPD, ribotyping), and its classification is confirmed;

It is GRAS (Generally Recognized as Safe);

It is already present at a rate of $10^8$ CFU/ml in the ProViva® product distributed by Skånemejerier and has been consumed since 1994;

It has a very good survival rate at an acid pH lower than 4;

It is amylase-negative and therefore does not degrade the texture of the end product.

However, this strain also has several disadvantages:

It has a strong post-acidification potential.

It results in significant organoleptic defects associated with acetic acid synthesis.

It degrades citric acid (e.g., lemon juice, orange juice) or malic acid (e.g., apple or pear juice), thus producing carbon dioxide gas, hence possible swelling problems, particularly if the cold chain is broken (i.e., going above the temperature of 8° C.).

Thus, this strain has numerous positive points, but it cannot be used as is in fruit-based food products, without depleting the organic acids of the fruit matrix on which the food product is based.

The same holds true for the strain of *Lactobacillus plantarum* deposited at the Collection Nationale des Cultures de Microorganismes on Apr. 4, 2002, under the number CNCM I-2845.

According to the invention, the term fruit matrix is understood to designate a fruit juice, a reconstituted fruit juice concentrate, or a fruit puree, without any probiotics, not depleted of organic acids, but optionally comprising other substances, e.g., such as sugar, water, flavourings, food colouring agents, sweetening agents, antioxidants, milk, preservatives, acidifiers, texturing agents, animal proteins (milk proteins, whey proteins . . . ) or vegetable proteins (soy, rice . . . ) or vegetable extract proteins (soy, rice . . . ).

The term off-tastes is understood to mean a taste that is abnormal for the food product. An off-taste is unpleasant to the consumer, and therefore not desirable. Thus, to illustrate, for the food product according to the invention, it is possible to cite the "earthy hay-like" off-taste resulting from the fermentation and oxidation of the product, the "vinegar-like" off-taste resulting from the organic acid ferment present in the product, and the "rancid" off-taste resulting from the presence of volatile fatty acids.

So-called "positive" notes can also be detected in the product, e.g., such as "orange" or "fruity" notes. Since these tastes are not unpleasant to the consumer, they are not included in the "off-tastes" according to this invention.

The concentration of molecules responsible for "off-tastes" is measured by solid phase microextraction (SPME) associated with gas chromatography (GC) coupled with a mass spectrometer (SM). This method was developed specifically and has enhanced sensitivity while at the same time having good reproducibility and good repeatability. SPME enables a specific concentration of the volatile target molecules for improved quantification and improved identification. CG enables separation of the volatile molecules based on the polarity and molar mass thereof, and thus obtainment of the peaks corresponding to each molecule. The concentration of each molecule is expressed in peak areas, i.e., in absorbance units (UA) proportional to their concentration in the sample. Finally, on the one hand, mass spectrometry enables positive identification of each molecule via the fragmentation thereof into characteristic ions, and, on the other hand, a second quantification of the volatile molecules wherein, this time, the concentration is expressed in mass units.

The term flavourings is meant to understand ingredients intended to give a flavour (i.e., a taste and/or an odour) to a foodstuff.

Flavourings are used for two primary objectives:

either they enhance the natural flavour of the food product, or partially restore it if it is too weak (products having lost a portion of their taste during the manufacturing process), or they replace an ingredient while introducing an aromatic note to the end product (e.g., strawberry flavoured yogurt).

According to this invention, the preferred flavourings are: apple, orange, red berries, strawberry, peach, apricot, plum raspberry, blackberry, currant, lemon, citrus fruits, grapefruit, banana, pineapple, kiwi, pear, cherry, coconut, passion fruit, mango, fig, rhubarb, melon, multi-fruits, exotic fruits, vanilla, chocolate, coffee and cappuccino.

The term (food) colouring agents is understood to mean substances capable of restoring or giving colouring to the food product.

According to this invention, the preferred colourings are: beta-carotene and carmine.

The term sweetening agent is understood to mean substances capable of mimicking the sweetening power of sugar without necessarily introducing the calories of sugar.

According to this invention, the preferred sweetening agents are: aspartame, Acesulfame-K, saccharine, sucralose and cyclamate.

The term antioxidants is understood to mean substances capable of preventing or reducing the oxidation phenomena which, among other things, cause the rancidification of fats or the browning of cut fruits and vegetables.

According to this invention, the preferred antioxidants are: vitamin C, vitamin E and rosemary extract.

The term milk is understood to mean milk of animal origin (e.g., cow, goat and ewe) or juices of vegetable origin (e.g., juice extracted from soybeans, tofu, rice, oats, quinoa, chestnuts, almonds or hazelnuts).

The term preservatives is understood to mean substances intended to assist in preservation by preventing the presence and development of undesirable microorganisms (for example: moulds or bacteria responsible for food poisoning) in the final food product.

According to the invention, the preferred preservatives are sorbic acid and sulphur dioxide.

The term texturing agents is understood to mean substances which make it possible to improve the presentation or behaviour of the final food product. The texturing agents can be emulsifiers, stabilizers, thickening agents or gel-forming substances. They can be used in the food product according to the invention alone or in combination.

According to this invention, the preferred texturing agents are: pectin, used as a gel-forming substance, carob seed, carrageenans, alginates, guar gum, xanthan gum, starch and mono- and diglycerides of edible fatty acids.

The term acidifiers is preferably understood to mean lactic acid and/or citric acid and/or phosphoric acid.

The term water is optionally understood to mean osmosis-purified water. Osmosis-purified water makes it possible to limit the amount of minerals present in the end product, since minerals can likewise be responsible for off-tastes.

Potassium, chlorine, magnesium and calcium are in fact rather bitter in various forms (KCl, NH₄CL, CaCl₂, Calcium acetate LiCl, MgSO₄ . . . ) whereas sodium, lithium and sulphate are rather salty and/or acidic depending on the form thereof (salty form: NaCl₂, Na₂SO₄, Na tartrate; acidic form: Na₂NO₃, Li acetate; salty and acidic form: Na acetate, Na ascorbate, Na citrate). Besides these direct effects on the sensory qualities of the products, these compounds can also have a "salting out" effect on the volatile molecules responsible for "smoky, phenolic . . . " off-tastes, by promoting the transition thereof to the gaseous phase above the product, thereby increasing the intensity of the off-tastes perceived.

According to this invention, the term organic acids is understood to designate, in particular, malic acid, citric acid, tartaric acid, pyruvic acid, fumaric acid or gluconic acid.

The organic acids the content of which is reduced or eliminated in comparison with the initial fruit matrix are preferably the malic and/or citric acids.

The initial organic acid content of the fruit matrix can be known from bibliographic sources. In the case where the fruit matrix is a fruit juice or a reconstituted fruit juice concentrate, the bibliographic references concern the organic acid concentration of the fruit juices. Such sources, for example, are the tables extracted from the AIJN "Code of Practice on Absolute Quality Requirements for Juices," such as the one presented herein below:

TABLE 1 extract from the AIJN "Code of Practice on Absolute Quality Requirements for Juices," showing the organic acid concentration of fruit juices.

|  | Citric acid (g/L) | L-malic acid (g/L) |
|---|---|---|
| Orange | 6.7-17 | 0.8-3 |
| Grapefruit | 8-20 | 0.2-1.2 |
| Apple | 50-200 | Min 3 |
| Grape | 0.5 max | 2.5-7 |
| Pineapple | 3-11 | 1.0-4.0 |
| Lemon | 45-63 | 1.0-7.5 |
| Passion fruit | 25-50 | 1.3-5.0 |
| Pear | 4 max | 0.8-5 |
| Apricot | 1.5-16 | 5-20 |
| Black currant | 26-42 | 1-4 |
| Morello cherry | 0.4 max | 15.5-27 |
| Raspberry | 9-22 | 0.2-1.2 |
| Strawberry | 5-11 | 0.6-5 |
| Peach | 1.5-5 | 2-6 |
| Mandarin orange | 6-22 | 0.5-3 |

In the case where the fruit matrix is not a fruit juice or a reconstituted fruit juice concentrate, the bibliographic sources concern the organic acid concentration of the fruits. Such sources, for example, are "La composition des aliments: tableaux des valeurs nutritives." 2000 (6ème Edition); Souci S. W.; Fachmann W.; Kraut H.; Scherz H., a sample table of which is reproduced herein below:

TABLE 2 organic acid concentration of fruits

|  | Citric acid (mg/100 g) | | | Malic acid (mg/100 g) | | |
|---|---|---|---|---|---|---|
| Fruit | Mean | Min | Max | Mean | Min | max |
| Pear | 140 | 80 | 200 | 170 | 100 | 240 |
| Strawberry | 748 | 670 | 940 | 303 | 90 | 340 |
| Peach | 240 | 160 | 320 | 330 | 280 | 370 |
| Pineapple | 630 | 580 | 670 | 94 | 87 | 100 |
| Grape | 23 | | | 327 | 220 | 650 |

TABLE 2-continued organic acid concentration of fruits

|  | Citric acid (mg/100 g) | | | Malic acid (mg/100 g) | | |
|---|---|---|---|---|---|---|
| Fruit | Mean | Min | Max | Mean | Min | max |
| Apple | 29 | 9 | 30 | 426 | 270 | 790 |
| Apricot | 400 | 140 | 700 | 1000 | 700 | 1300 |
| Orange | 1042 | 600 | 1880 | 89 | 40 | 190 |
| Banana | 201 | 80 | 390 | 360 | 240 | 500 |
| Mango | 264 | 200 | 327 | 74 | | |
| Morello cherry | 4.7 | | | 1800 | | |
| Cherry (sweet) | 13 | 10 | 15 | 940 | 730 | 1110 |
| Plum | 34 | 23 | 55 | 1220 | 820 | 1990 |
| Prune | 158 | | | 5690 | | |
| Blackberry | 18 | 15 | 21 | 900 | 860 | 950 |
| Blueberry | 523 | | | 850 | | |
| Raspberry | 1720 | 1060 | 2480 | 400 | 0 | 800 |
| Grapefruit | 1296 | 1000 | 1460 | 180 | 50 | 310 |
| Guava | 537 | 532 | 541 | 325 | 182 | 469 |
| Kiwi | 995 | 980 | 1010 | 500 | 470 | 530 |
| Passion fruit | 3250 | | | 650 | | |
| Papaya | 54 | 29 | 100 | 29 | 27 | 31 |
| Lemon | 4683 | 3500 | 7200 | 200 | | |
| Quince | | | | 930 | | |
| Rosehip | | | | 3100 | | |
| Lychee | 16 | | | 239 | | |
| Pomegranate | 500 | | | 100 | | |
| Melon | 75 | 0 | 150 | | 0 | 50 |

In both cases, the value from the table that is used to determine the initial organic acid content of the fruit juices or fruits is the minimum value.

Furthermore, the initial organic acid content of the fruit matrix can be defined by any appropriate quantification method.

Such methods are, for example:

Measurement of the titratable acidity, which quantifies concentration of acids present in the fruit matrix. This consists in neutralizing a sample of the fruit matrix with a 0.1N sodium hydroxide solution, the amount of sodium hydroxide required in order to reach a pH level of 8, thereby making it possible to deduct the total acidity value.

Chromatographic assay using HPAEC (High Performance Anion Exchange Chromatography) (Dionex method: 164-166 avenue Joseph Kessel 78960 Voisins Le Bretonneux France) coupled with conductimetric detection.

The malic and citric acids can be assayed via enzymatic methods; the reference methods are advocated by the International Federation of Fruit Juice Producers (IFU) (these references have been established since 1985): IFU 21 for malic acid and IFU 22 for citric acid; these are spectrophotometric methods which involve enzyme reactions.

The IFU 21 method operates on the following principle: the citric acid (citrate) initially present in the fruit matrix is converted into oxaloacetate and acetate in the reaction catalyzed by the citrate lyase enzyme CL (1).

(1) Citrate  oxaloacetate + acetate

In the presence of the L-malate dehydrogenase and L-lactate dehydrogenase enzymes, the oxaloacetate and pyruvate produced via decarboxylation, are reduced to L-malate and L-lactate, respectively, by Nictinamide Adenine Dinucleotide (NADH) (2) (3)

The amount of NADH oxidized in the reactions (2) and (3) is stoichiometric with the amount of citrate. NADH is determined by measuring the light absorbency thereof at 334, 340 or 365 nm. This measurement made it possible to determine the amount of citric acid initially present in the fruit matrix.

The IFU 22 method operates on the following principle: the L-lactic acid (L-lactate) initially present in the fruit matrix is oxidized into pyruvate with Nicotinamide Adenine Dinucleotide (NAD) in the presence of L-lactate dehydrogenase (L-LDH) (1).

The equilibrium for this reaction rests on the L-lactate side. By trapping the pyruvate in a subsequent reaction catalyzed by the glutamic-pyruric transaminase (GPT) enzyme in the presence of L-glutamate, the equilibrium can be shifted in favour of the pyruvate and NADH (2).

The amount of NADH formed in the previous reaction is stoichiometric with the amount of L-lactic acid. The increase in NADH is determined by measuring the light absorbency thereof at 334, 340 or 365 nm. This measurement makes it possible to determine the amount of L-lactic acid initially present in the fruit matrix.

According to a first aspect of the invention, the food product can be a beverage, preferably containing fruit juices or reconstituted concentrate-based fruit juices.

According to this invention, the following can be cited as fruit juices: orange juice, and in particular 10-12° Brix NFC (Not from Concentrate) and, as a reconstituted orange juice concentrate, FCOJ (Frozen Concentrate Orange Juice) at 66° Brix, and the other fruit juice concentrates at between 10 and 70° Brix.

According to this invention, the food product contains between 20 and 99.99% fruit juices, and preferably between 50 and 99.99% fruit juices.

According to a second aspect of this invention, the food product can be a fruit-based puree preferably comprising between 50 and 99.99% fruit purees and more preferably yet between 90 and 99.99% fruit purees.

According to this invention, the probiotics are at a concentration of between $5 \cdot 10^5$ and $1 \cdot 10^8$ CFU/ml, and preferably at a concentration greater than or equal to $10^8$ CFU/ml. The concentration is most preferably $4 \cdot 10^7$ CFU/ml.

According to the invention, the food product has a pH of between 3 and 4.

According to this invention, the food product keeps, and can therefore be consumed, for at least 30 days at a maximum temperature of 10° C., without requiring the addition of bacteriostatic agents.

According to this invention, the food product is one fruit-based.

According to this invention, the food product is based on several fruits.

According to this invention, the fruit or fruits have a high organic acid content.

According to this invention, the fruits are: orange, lemon, grape, pineapple, apple, pear, peach and/or red berries.

According to this invention, the food product preferably contains milk and/or vegetable juice.

The vegetable juice is preferably a juice made from soybean (juice extracted from soybeans and/or tofu).

According to this invention, the organic acids preferably eliminated from the fruit matrix are malic acid, citric acid, tartaric acid, pyruvic acid, fumaric acid, gluconic acid, p. coumaric and/or caffeic acid.

A second object of this invention is a method of preparing a food product according to this invention, characterised in that it includes the following steps:
 a) Depletion of organic acids from the fruit-based matrix,
 b) Addition of probiotics to the matrix obtained after step a),
 c) Packaging of the product obtained after step b).

According to this invention, step a) for depleting organic acids from a fruit-based matrix is carried out by selecting a fruit matrix having low natural acidity.

According to this invention, the term fruit matrix having low natural acidity is understood to designate a fruit matrix from which a naturally low-acid juice is obtained, the acidity of which is between the low value indicated in the AIJN "Code of Practice," (The Association of the Industry of Juice and Nectars from Fruits and Vegetables of the European Union) recognized by all professionals in the field of fruit juices, and −50% of this value.

Natural acidities depend not only on the fruit, but also on the variety thereof, the climate and the time of harvesting. Consequently, ranges of acidity per fruit are defined and the values are shown in the table below: (source: AIJN):

TABLE 3

| ranges of acidity for fruit, according to the AIJN | |
|---|---|
| Fruits | Titratable acidity (expressed in g of anhydrous citric acid per litre of juice, measured at pH 8.1 |
| Orange | 5-15 |
| Grapefruit | 7.7-18.5 |
| Apple | 2.2-7.5 |
| Grape | 4-11 |
| Pineapple | 3.2-11.5 |
| Lemon | 44.8-62 |
| Passion fruit | 25.6-50 |
| Pear | 1.4-7 g/kg |
| Apricot | 6.4-19.2 g/kg |
| Currant | 26.7-40.1 |
| Sour cherry | 12.8-22.6 |
| Raspberry | 12.2-20 |
| Strawberry | 5.1-11.5 |
| Peach | 3.2-8 g/kg |
| Banana | 2-3.8 |
| Mandarin orange | 5.8-19.2 |

As concerns the orange, the varieties found to have low natural acidity can have an acidity level of 3, for example, (i.e., 40% below the low value of the range).

According to this invention, the selection of a fruit matrix having a low natural acidity is carried out via varietal selection of the fruits and/or by controlling the ripening of the fruit.

The fruits will preferably be selected as soon as they have reached late maturity.

According to this invention, step a) for depleting organic acids from a fruit-based matrix is carried out via de-acidification of the fruit matrix.

According to this invention, de-acidification (reduction in titratable acidity) of the fruit matrix is carried out via electrodialysis of the fruit matrix, precipitation of the organic acids from the fruit matrix with calcium salts, malolactic fermentation, selective assimilation of the citric acid and/or passing the fruit matrix over an anion exchange resin.

Citric fermentation results in the production of diacetyl and acetoin via lactic bacteria.

De-acidification of the fruit matrix according to the invention is preferably carried out via electrodialysis and/or passage of the fruit matrix over an anion exchange resin.

As a matter of fact, an anion exchange resin is ideal for collecting compounds which have COOH acid radicals, since these radicals are easily separated into COO$^-$ (anion) and H$^+$ (cation), and said resin is therefore suitable for collecting organic acids.

The anion exchange resins used, for example, can consist of Dowex® 1 resins supplied by Dow Chemical, USA and Amberlite® IRA-402 resins supplied by Rohm and Haas Co., USA.

According to this invention, the probiotics are incorporated as part of a delayed differentiation process, i.e., at the end of the production line and immediately before or during the packaging step.

Furthermore, step b) and step c) according to this invention can be carried out simultaneously. In this hypothetical case, the method according to the invention only has two steps for preventing alterations of the final food product during storage thereof, without any proliferation of microorganisms.

In one preferred embodiment, a step for adding lactic acid is carried out between step b) and step c) of said method, or simultaneously therewith. The amount of lactic acid to be added will be easily determined by those skilled in the art, based on the desired strain of bacteria to be used.

EXAMPLES

Example 1

Formation of gases by the *L. plantarum* DSM 9843 and *L. plantarum* 1-2845 strains (deposited at the CNCM on Apr. 4, 2002) in relation to the inoculated fruit juice.
Material and Methods:
I.1. Preparation of the Bacterial Suspensions and Inoculation of the Fruit Juices A first 2-mL pre-culture is made with the DSM 9844 and I-2845 strains. This pre-culture serves to seed 100 mL of 1% neutral SRM (i.e., $10^8$-$10^9$ CFU/mL). From this second pre-culture, 3×1,000 mL neutral SRM (i.e., $10^8$-$10^9$ CFU/mL) are seeded.

Centrifuging (Beckman JA-25, rotor JA-10) is carried out for each strain, as follows, using 500-mL bowls:
  filling 6 bowls with 330 mL of culture,
  centrifuging for 10 min, 12,000 g, 20° C.,
  elimination of the supernatant and addition of 165 mL of culture,
  centrifuging for 10 min, 12,000 g, 20° C.,
  elimination of the supernatant.

Each pellet obtained is then taken up again separately in the fruit juice being tested, and the suspension obtained is put back into the fruit juice brick carton, which is then closed back up again carefully.
I.2. Organic Acid Assays The chosen technique consists in separating the organic acids via high performance anion exchange chromatography (HPAEC). Detection of the organic acids is carried out by suppressive conductimetric detection (SCD).

The chromatographic system used is of the DIONEX brand (DX600 type) comprising a suppressive conductimetric detection system. The thermostatically controlled conductimetric cell (DS3 type) is coupled to an external self-suppression system ASRS-ULTRA (4 mm). This electrolytic suppressor was used with a Milli-Q counter-current water recirculation means, at a flow rate of 4 mL/min (approximate pressure of 15 psi).

An AS11-HC-type (4 mm) anion exchange column is associated with an AG11-HC-type guard column. The elution flow rate is 1.5 mL/min.
II Results:
II.1. Bacterial Counts Bacterial counts are carried out during storage of the products, so as to evaluate the survival of *L. plantarum* during storage of the fruit juices at 10° C.

TABLE 4

Bacterial counts of *L. plantarum* during storage of the fruit juices at 10° C.

| Strain | Time (d) | Orange | Apple | Grape |
|---|---|---|---|---|
| DSM 9843 | D0 | 1.8·$10^9$ CFU/mL | 1.7·$10^9$ CFU/mL | 9.5·$10^8$ CFU/mL |
| | D5 | 5.0·$10^9$ CFU/mL | 5.8·$10^8$ CFU/mL | 4.1·$10^9$ CFU/mL |
| I2845 | D0 | 1.1·$10^9$ CFU/mL | 9.8·$10^8$ CFU/mL | 6.0·$10^8$ CFU/mL |
| | D5 | 4.5·$10^9$ CFU/mL | 1.6·$10^9$ CFU/mL | 3.9·$10^9$ CFU/mL |

II.2. Demonstration of the Consumption of Organic Acids During Storage.

The organic acid assays were carried out at 0 and 5 days, at the same time as the counts, and the results are summarized in Table 4.

TABLE 5

Metabolites produced and organic acids consumed when the fruit juice containing *L. plantarum* was stored at 10° C.

| | Batches | | Swelling of the bottle | pH | Lactate produced mmol | Acetate produced mmol | Malate consumed mmol | Citrate consumed mmol |
|---|---|---|---|---|---|---|---|---|
| Apple juice | Control | D 0 | — | 3.43 | 0.00 | 0.00 | 0.00 | 0.00 |
| | + DSM 9843 | D 5 | ++ | 3.38 | 27.93 | 4.44 | 6.72 | 0.21 |
| | + I-2845 | D 5 | ++ | 3.39 | 40.86 | 4.38 | 21.20 | 0.19 |

TABLE 5-continued

Metabolites produced and organic acids consumed when the fruit juice containing *L. plantarum* was stored at 10° C.

| | Batches | | Swelling of the bottle | pH | Lactate produced mmol | Acetate produced mmol | Malate consumed mmol | Citrate consumed mmol |
|---|---|---|---|---|---|---|---|---|
| Orange juice | Control | D 0 | – | 3.34 | 0.00 | 0.00 | 0.00 | 0.00 |
| | + DSM 9843 | D 5 | +++ | 3.26 | 53.79 | 25.78 | 11.99 | 4.91 |
| | + I-2845 | D 5 | ++ | 3.27 | 48.90 | 15.60 | 13.26 | 1.42 |
| Grape juice | Control | D 0 | – | 3.22 | 0.00 | 0.00 | 0.00 | 0.00 |
| | + DSM 9843 | D 5 | ++ | 3.23 | 40.79 | 10.38 | 23.50 | 2.09 |
| | + I-2845 | D 5 | +++ | 3.24 | 44.59 | 8.16 | 33.87 | 1.43 |

According to the results presented in Table 5, it is quite apparent that malic acid is the substrate most heavily consumed by *L. plantarum*, regardless of the strain involved. This consumption is not only accompanied by production of lactate and acetate, and thus a noticeable decrease in the pH level (particularly in orange and apple juice) but also a production of gas which has a macroscopic effect on the packaging.

According to the metabolic pathways presented in FIG. 1, the absence of detection of formate production (no pyruvate formate-lyase action), the very low pentose content in the fruit juices treated, the following batch reconciliation of $CO_2$ (expressed in moles) can be proposed:

Total $CO_2$=malate consumed+citrate consumed+(total acetate produced−citrate-derived acetate).

Thus, by replacing the acetate produced from the citrate by the amount of consumed citrate:

Total $CO_2$=malate consumed+total acetate produced.

CONCLUSION

Thus, malic acid and, to a lesser extent, citric acid contribute heavily to the production of gases when fruit juices containing a high dose (>1·10$^9$ FCU/mL) of DSM 9843 or 1-2845 *L. plantarum* bacteria.

Example 2 dilution of orange juices in order to define the maximum concentrations of organic acids compatible with *L. plantarum* in relation to the percentage of juice in the formula.

We made dilutions with 5, 10, 20 and 30% orange juice, these dilutions corresponding to the de-acidification rates of 95, 90, 80 and 70%.

TABLE 6

| % of juice in the product | % of de-acidification | pH | Swelling observed? |
|---|---|---|---|
| 30% | 70% | Natural pH | Swelling at D + 3 |
| 30% | 70% | 3.7 | Swelling at D + 5 |
| 20% | 80% | Natural pH | Slight swelling at D + 14 |
| 20% | 80% | 3.7 | Very slight swelling |
| 10% | 90% | Natural pH | No |
| 10% | 90% | 3.7 | No |

TABLE 6-continued

| % of juice in the product | % of de-acidification | pH | Swelling observed? |
|---|---|---|---|
| 5% | 95% | Natural pH | No |
| 5% | 95% | 3.7 | No |

In order for an orange juice-based beverage containing *L. plantarum* to be stable more than 30 days after the manufacture thereof, we determined that it was necessary for it to have the following characteristics:

TABLE 7

| % of orange juice in the beverage | Acidity of the orange juice | Brix/acidity ratio |
|---|---|---|
| 100 | 0.4-0.6 | 100-150 |
| 75 | 1.3-1.45 | 41-46 |
| 50 | 2.2-2.3 | 27-30 |

Comments:
the "Brix/acidity ratio" designates the ratio of the Brix value of the juice to the number of grams of anhydrous citric acid per 100 grams of juice; (Brix/acid ratio).
the "Brix value" designates the sugar content determined by refractometry, to which the acidity correction is added, according to the method of the Association of Official Analytical Chemistry of the United States, entitled "Solids (Soluble) in Fruit Products," published in *Official Methods of Analysis of the Association of Official Analytical Chemistry*, 14$^{th}$ Edition, 1984. (Brix content) DORS/88-8, art. 2; DORS/95-548, art. 2; DORS/2000-184, art. 27; DORS/2003-6, art. 65 (F).

Example 3

Sensory Analysis of Various Products

Subsequent to the technical problems of using the DSM 9843 strain in plant environments (production of $CO_2$ via the metabolization of malic and/or citric acid, resulting in swelling of the UHT brick cartons; production of off-tastes due to the presence of organic acids and the metabolization of phenolic acids), the following technical solutions were tested:
1) De-acidification of the juices on ion-exchange resins,
2) Use of osmosis-purified water (to evaluate the impact of minerals on off-tastes), 3) Use of various types of acids for acidification: lactic acid, citric acid or phosphoric acid.

7 tests were conducted from all of these hypotheses:

TABLE 8

| Tests | Type of orange juice (24%) | Presence of milk (16%) | Type of acid for pH 3.8 |
|---|---|---|---|
| SLC | Standard juice | Yes (L) | Citric acid (C) |
| DLC | De-acidified juice (D) | Yes | Citric acid |
| SLL | Standard juice | Yes | Lactic acid (L) |

TABLE 8-continued

| Tests | Type of orange juice (24%) | Presence of milk (16%) | Type of acid for pH 3.8 |
|---|---|---|---|
| DLL | De-acidified juice | Yes | Lactic acid |
| DLL (osmosis-purified) | De-acidified juice | Yes | Lactic acid |
| DL | De-acidified juice | No | Lactic acid |
| LL | No juice | Yes | Lactic acid |

Results:

TABLE 9

| MIX | Type of acid | Test | Flavours at Day 0 | Flavours at D 30 | BALANCE SHEET |
|---|---|---|---|---|---|
| Standard juice | + milk | + citric acid | SLC | "Juice" notes +++ off-tastes − | "Juice" notes + off-tastes +++ (hay, soil, stable) | ↓ "Juice" notes ↑↑↑ off-tastes |
| | + milk | + lactic acid | SLL | "Juice" notes +++ off-tastes − | "Juice" notes + off-tastes +++ (hay, soil, stable) | ↓ "Juice" notes ↑↑↑ off-tastes |
| De-acidified juice | + milk | + citric acid | DLC | "Juice" notes +++ off-tastes − | "Juice" notes − off-tastes +++ (vinegar) | ↓ "Juice" notes ↑↑↑ off-tastes |
| | + milk | + lactic acid | DLL | "Juice" notes − off-tastes −− | "Juice" notes − off-tastes + (rancid) | No "juice" notes ↑ off-tastes |
| | + milk | + lactic acid | Osmosis-purified DLL | "Juice" notes − off-tastes −− | "Juice" notes − off-tastes − (somewhat fruity juice) | No "Juice" notes no off-tastes |
| | + milk | + lactic acid | DL | "Juice" notes +++ off-tastes −−− | "Juice" notes − off-tastes − (somewhat fruity juice) | ↓ "Juice" notes no off-tastes |
| Milk | + lactic acid | | LL | "Juice" notes −− off-tastes −− | "Juice" notes −− off-tastes −−− (very fruity/floral) | No "juice" notes no off-tastes |

Comment: the flavours are evaluated from − (very weak intensity for this flavour) to +++ (very strong intensity for this flavour). A downward arrow in the table (↓) indicates a reduction, an upward arrow (↑) an increase, and three upward arrows (↓↓↓) a significant increase in the positive and/or negative aromatic notes ("juice" notes) (off-tastes) for the juice.

Generally speaking, even though citric acid strengthens the "orange juice" notes in the products from D0 to D30, all of the products lose these organoleptic characteristics and are relative neutral as concerns the fruity/orange notes.

From a metabolic perspective, citric acid is indeed a precursor of off-tastes, because this acid is metabolized by *Lactobacillus plantarum* in order to form acetic acid (in the case of de-acidified juice) or ethyl phenol (in the case of standard juice). Consequently, the addition of citric acid should be as small as possible in order to prevent the formation of these molecules, while at the same time having a positive effect on the "juice" notes.

With regard to the type of juice, the de-acidification of juices is a method that makes it possible to prevent the formation of off-tastes (except in the presence of citric acid) and only rancid notes persist, primarily due to the presence of milk. Consequently, an adjustment in the de-acidified juice/milk ratio should be made.

Finally, the best results, in terms of an absence of off-tastes (hay, stable, soil, vinegar, rancid) and the presence of aromatic notes characteristic of orange juice, are obtained with de-acidified juiced mixed with osmosis-purified water and acidified with lactic acid.

Example 4

Fruit Juice+Milk Formula

TABLE 10

| Orange fruit juice + milk product at a target pH of 3.8 | |
| --- | --- |
| Water | Approximately 70% |
| Sugar | Approximately 7.5% |
| De-acidified orange juice concentrate | Approximately 4.5% |
| Orange flavour | 0.0054% |
| Pectin | 0.56% |
| Beta-carotene | 0.09% |
| Milk | Approximately 16.5% |

TABLE 10-continued

| Orange fruit juice + milk product at a target pH of 3.8 | |
| --- | --- |
| Lactic acid | Final pH 3.8 |
| *Lactobacillus plantarum* DSM 9843 | Seeded at 0.1% |

Example 5

50% and 750 Orange Juice Formulas

TABLE 11

| 50% Orange fruit juice at a target pH of 3.6 | |
| --- | --- |
| Water | 80.4 |
| Sugar | 3.5 |
| De-acidified orange juice concentrate | 11 |
| Pulp | 3.7 |
| Pectin | 0.2 |
| Food colouring agent | 0.02 |
| Lactic acid | 0.4 |
| Ascorbic acid | 0.03 |
| Strain of *L. plantarum* DSM 9843 | Seeded at 0.1% |

TABLE 12

| 75% Orange fruit juice at a target pH of 3.6 | |
| --- | --- |
| Water | 80.2 |
| Sugar | 1.3 |
| De-acidified orange juice concentrate | 13.4 |
| Pulp | 3.9 |
| Pectin | 0.2 |
| Food colouring agent | 0.02 |
| Lactic acid | 0.13 |
| Ascorbic acid | 0.03 |
| Strain of *L. plantarum* DSM 9843 | Seeded at 0.1% |

The invention claimed is:

1. A biologically pure strain of *Lactobacillus plantarum* deposited at the Collection Nationale des Cultures de Microorganismes on Apr. 4, 2002, under the number CNCM I-2845.

* * * * *